United States Patent [19]

Akhavi

[11] 4,240,423

[45] Dec. 23, 1980

[54] AUTOCLAVABLE TRANSPARENT NEEDLE

[75] Inventor: David S. Akhavi, Los Angeles, Calif.

[73] Assignee: American Hospital Supply Corporation, Evanston, Ill.

[21] Appl. No.: 953,605

[22] Filed: Oct. 23, 1978

[51] Int. Cl.³ ............................................. A61M 5/32
[52] U.S. Cl. ............................... 128/218 N; 128/221
[58] Field of Search ............... 128/221, 218 N, 218 R, 128/215, 216

[56] References Cited

U.S. PATENT DOCUMENTS 3,093,134  6/1963  Roehr .................................. 128/221
3,186,408  6/1965  Jacob .................................. 128/221

OTHER PUBLICATIONS

Mitsui Petrochemical Ind. Ltd. "A Timely Injection".

*Primary Examiner*—John D. Yasko
*Attorney, Agent, or Firm*—Larry N. Barger

[57] ABSTRACT

A hypodermic needle having a cannula secured to a transparent polycarbonate hub having a deflection temperature of approximately 270° to 290° F., which needle is autoclavable in the range of approximately 240° to 260° F. without substantial distortion.

7 Claims, 3 Drawing Figures

AUTOCLAVABLE TRANSPARENT NEEDLE

BACKGROUND

It has been proposed in the past to use a transparent needle hub of cellulose acetate material molded to a metal cannula as described in U.S. Pat. No. 3,093,134. This transparent hub gave a visual indication of notches, etc. in an embedded rear portion of the cannula corresponding to the beveled forward end of the cannula. Thus, a nurse or physician could determine the cannula's beveled position when the forward end of the cannula was embedded in a patient.

While the above needle hub was transparent, it had a disadvantage in that the cellulose acetate material had a very low deflection temperature, i.e. it would distort at approximately 131° F. The hub could possibly reach such temperatures when left in an automobile on a very hot summer day or in certain sections of a warehouse without air conditioning in certain desert climates. Even if this needle hub only reached temperatures of approximately 120° F., such exposure may slightly vary the dimensions of the hub's internal taper so that it no longer made a good sealing fit with a tapered adapter of a syringe barrel. The applicant has no knowledge that the needle hub described in U.S. Pat. No. 3,093,134 was ever marketed.

Because of the strenuous stresses required in a needle hub that is forcefully wedged onto a syringe barrel, the material of the hub is very critical. Hubs have frequently been made of metal, including aluminum and stainless steel, as well as nylon. Hubs have also been make of polypropylene, but polypropylene hubs are at best only cloudy and translucent with less than 50% light transmission.

The metal hubs which were crimped onto the metal cannula were autoclavable, but were certainly not transparent. The prior nylon hubs were not autoclavable (steam sterilizable) because nylon absorbs substantial amounts of water from the steam and the nylon hubs change dimensions with autoclaving.

A transparent needle hub is highly desirable because it permits the nurse or physician making a puncture into an artery or a vein to observe blood immediately as it arrives at the rear end of the metal cannula. Thus, he can obtain a quicker indication of whether the cannula is properly located in the vein or artery. Previously the blood had to fill the cannula, opaque needle hub, syringe adapter, and enter, the main barrel portion before it became visible. Most of the syringe's tapered adapter was covered by the opaque needle hub.

The transparent hub is useful during a hypodermic injection so the nurse or physician can see any air bubbles and expel them before injection. Air bubbles are highly undesirable during injection.

To applicant's knowledge, there has never been a needle on the market which had a hub that is both transparent and autoclavable at temperatures of 240° to 260° F. Needles, such as with metal hubs, are frequently inserted in a tray of assembled instruments in a hospital and the entire tray autoclaved for sterilization immediately prior to surgery.

SUMMARY OF THE INVENTION

The present invention provides a hypodermic needle with a cannula secured to a thermoplastic hub that is both autoclavable and highly transparent. The hub is of a polycarbonate material having a deflection temperature (approximately 270° to 290° F.) which is higher than needed for autoclaving.

A related application entitled, "Needle Identification System," Ser. No. 953,606, filed Oct. 23, 1978, has to do with identifying cannula gauge sizes in a hypodermic needle.

THE DRAWINGS

DETAILED DESCRIPTION

Figure 1:
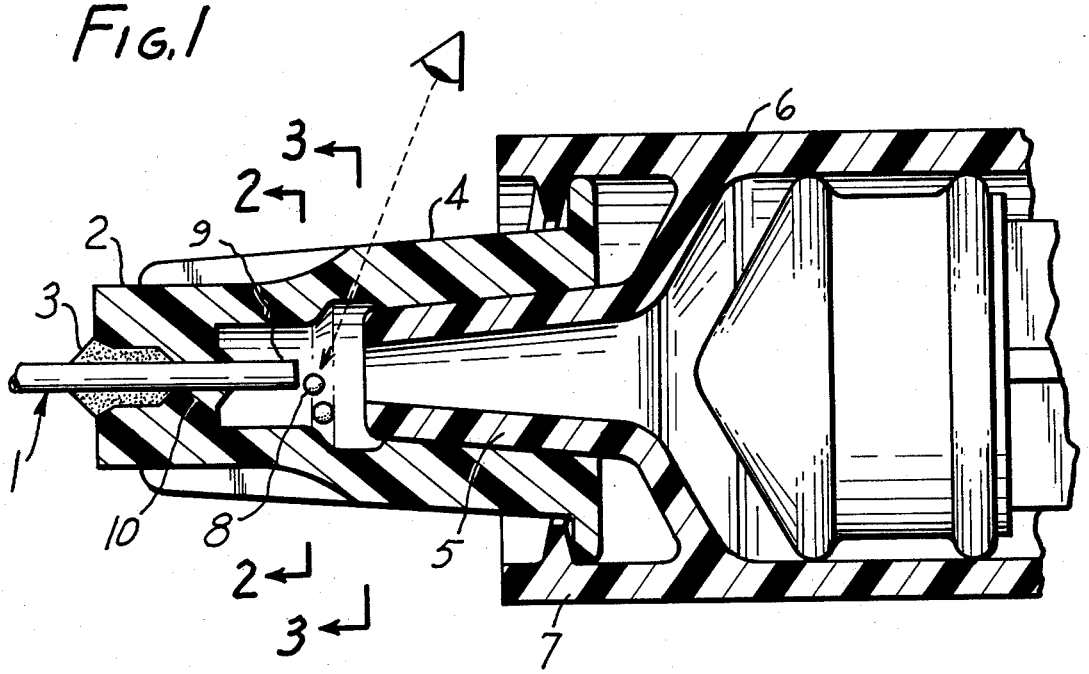
FIG. 1 is a fragmentary sectional view of the needle of this invention attached to a hypodermic syringe.

In FIG. 1, a hypodermic needle is shown with a conventional metal cannula 1 which normally would have a beveled forward end (not shown). To this cannula is secured a transparent polycarbonate hub 2. Securement is made by an epoxy-type adhesive 3 that is capable of withstanding steam sterilization temperatures of 240° to 260° F. This epoxy is heat curable in a temperature range of 200° to 290° F.

The polycarbonate needle hub 2 has an internal tapered section 4 that wedgingly fits on a needle adapter 5 of a syringe 6. A threaded locking collar 7 can be used, if desired, to help hold the needle to the adapter 5.

As schematically shown, blood droplets 8 are immediately visible through transparent hub 2 as they drift from a rear portion 9 of cannula 1. As shown in FIG. 1, a rear portion 9 protrudes from a front wall section 10 of the hub. Due to manufacturing tolerances, there may or may not be such a protrusion.

Figure 2:
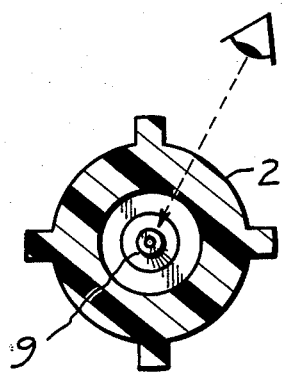
FIG. 2 is a sectional view along line 2—2 of FIG. 1.
Figure 3:
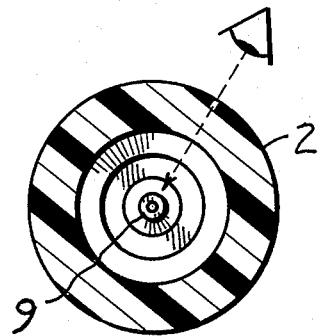
FIG. 3 is a sectional view taken along line 3—3 of FIG. 1.

FIGS. 2 and 3 further illustrate the visibility of the interior of the hub from different portions of the hub immediately forward of the syringe's needle adapter.

Autoclaving is frequently carried out at temperatures in the range of 240° to 260° F., but might be carried out at temperatures slightly below this range over an extended period of time. However, autoclaving would not be carried out at temperatures below 200° F., which is well above the deflection temperature of 131° F. of the prior art cellulose acetate transparent thermoplastic hub.

Polycarbonate has an extremely high transparency and is actually used to make thermoplastic optical lenses. The applicant's polycarbonate hub described in this invention actually looks to the naked eye as if it is made of glass. It is much more transparent than the somewhat translucent barrel of conventional syringes made of polypropylene. The polycarbonate hub transmits at least 80% of light impinging upon the hub, and normally will transmit approximately 88% of the light.

The polycarbonate hub has been tested and does withstand the large amount of stresses in the wedge fit to the syringe barrel's adapter without cracking or crazing. In certain structural configurations, polycarbonate does stress, crack or craze. However, the applicant has found in the present invention that the polycarbonate hub does not stress, crack or craze.

At autoclave temperatures of 240° to 260° F. with the polycarbonate hub, with a deflection temperature of approximately 270° to 290° F. according to ASTM standard test procedure, the hub is admittedly on the borderline of being autoclavable. The applicant has unexpectedly found that the polycarbonate hub is autoclavable, and withstands the rigorous stresses of a needle hub configuration without stress cracking and had high transparency. To applicant's knowledge, a needle with such a hub has never been made or described in the past, even though transparent polycarbonate materials have been available for approximately 20 years.

The metal cannula 1 is secured to the polycarbonate hub by an epoxy which can also stand the autoclaved temperatures. There are many different epoxies that could stand the temperature and the present epoxy has been selected as being heat curable in the range of 240° to 260° F. Such an epoxy must reach this temperature range before it obtains its maximum strength and is cured. Temperatures slightly above its cure range would not materially affect its strength. An epoxy that works well is a bisphenol type epoxy marketed by Dow Chemical under the catalog number DER .332.

In the foregoing description, a specific example has been used to describe the invention. However, it is understood by those skilled in the art that modifications could be made to this example without departing from the spirit and scope of the invention.

I claim:

1. An autoclavable needle comprising: a metal cannula; an epoxy capable of firmly bonding at temperatures in excess of 200° F., which epoxy is permanently secured to the cannula; and permanently secured to this epoxy is a transparent polycarbonate hub having a deflection temperature in excess of 200° F., whereby both the metal-epoxy joint and the epoxy-polycarbonate joint remain firm when exposed to temperatures in excess of 200° F.

2. A needle as set forth in claim 1, wherein the cannula is secured to the hub with an adhesive that is heat curable at temperatures in excess of 200° F.

3. A needle as set forth in claim 1, wherein the hub has a light transmission of at least 80%.

4. A needle as set forth in claim 1, wherein the hub is polycarbonate.

5. An autoclavable needle comprising: a metal cannula; a transparent polycarbonate hub having a deflection temperature in the range of 240° to 290° F.; a high temperature epoxy permanently securing together the cannula and hub, which epoxy is capable of firmly bonding at temperatures in the range of 240° to 290° F., whereby both the metal-epoxy joint and the epoxy-polycarbonate joint remain firm when exposed to temperatures in the range of 240° to 290° F.

6. A needle as set forth in claim 5, wherein the needle is autoclavable at temperatures of 240° to 260° F. without substantial distortion.

7. A needle as set forth in claim 5, wherein the polycarbonate hub has an internally tapered section adapted to wedgingly fit on an externally tapered adapter of a syringe and withstands the normal stresses of such wedged joint without substantial crazing.

* * * * *